United States Patent
Kim et al.

(10) Patent No.: US 10,539,543 B2
(45) Date of Patent: Jan. 21, 2020

(54) CHIP-TYPE PARTICULATE MATTER SENSOR

(71) Applicant: HYUNDAI MOTOR COMPANY, Seoul (KR)

(72) Inventors: Dong-Gu Kim, Suwon-si (KR); Sang-Hyeok Yang, Suwon-si (KR)

(73) Assignee: Hyundai Motor Company, Seoul (KR)

( * ) Notice: Subject to any disclaimer, the term of this patent is extended or adjusted under 35 U.S.C. 154(b) by 221 days.

(21) Appl. No.: 15/376,272

(22) Filed: Dec. 12, 2016

(65) Prior Publication Data
US 2018/0156709 A1 Jun. 7, 2018

(30) Foreign Application Priority Data
Dec. 7, 2016 (KR) ........................ 10-2016-0165960

(51) Int. Cl.
| | | |
|---|---|---|
| *G01N 33/00* | (2006.01) | |
| *G01N 15/06* | (2006.01) | |
| *G01N 15/00* | (2006.01) | |

(52) U.S. Cl.
CPC ..... *G01N 33/0036* (2013.01); *G01N 15/0606* (2013.01); *G01N 15/0656* (2013.01); *G01N 2015/0046* (2013.01)

(58) Field of Classification Search
CPC ........... G01N 15/0606; G01N 15/0656; G01N 2015/0046; G01N 33/0036
USPC ......... 73/23.31, 28.01, 23.33, 114.71, 31.02, 73/31.03
See application file for complete search history.

(56) References Cited

U.S. PATENT DOCUMENTS

| | | | | |
|---|---|---|---|---|
| 4,456,883 A * | 6/1984 | Bullis | ................... | G01N 27/62 324/130 |
| 4,597,850 A * | 7/1986 | Takahasi | ............ | G01N 27/4077 204/426 |
| 4,929,331 A * | 5/1990 | Kato | ................... | G01N 27/4077 204/426 |
| 5,651,248 A * | 7/1997 | Kawamura | ........ | B01D 46/0063 55/283 |
| 6,279,376 B1 * | 8/2001 | Yamada | ............. | G01N 27/4077 73/23.2 |
| 6,780,298 B2 * | 8/2004 | Nakamura | ......... | G01N 27/4077 204/428 |
| 7,168,292 B2 * | 1/2007 | Gundel | .................... | G01N 5/02 73/24.02 |
| 7,575,663 B2 * | 8/2009 | Nakamura | ......... | G01N 27/4077 204/424 |

(Continued)

FOREIGN PATENT DOCUMENTS

| | | |
|---|---|---|
| JP | 2011-256796 A | 12/2011 |
| JP | 5201193 B2 | 6/2013 |
| KR | 10-1401713 B1 | 6/2014 |

*Primary Examiner* — Jonathan M Dunlap
(74) *Attorney, Agent, or Firm* — Knobbe Martens Olson & Bear LLP

(57) ABSTRACT

A chip-type PM (Particulate Matter) sensor comprising a sensing unit installed in a cylindrical housing mounted on an exhaust pipe, the sensing unit having a sensing pattern for sensing particulate matters contained in exhaust gas, wherein the sensing unit may include a substrate formed in a direction perpendicular to the longitudinal direction of the housing, and the sensing pattern formed on a surface of the substrate, facing the exhaust pipe, and configured to sense the particulate matters.

6 Claims, 13 Drawing Sheets

(56) References Cited

U.S. PATENT DOCUMENTS

| | | | | |
|---|---|---|---|---|
| 7,739,898 B2* | 6/2010 | Shaddock | F01N 13/08 | |
| | | | 73/23.31 | |
| 8,225,640 B2* | 7/2012 | Nelson | G01N 15/0656 | |
| | | | 73/28.01 | |
| 8,915,119 B2* | 12/2014 | Ueno | F01N 9/002 | |
| | | | 73/23.33 | |
| 8,966,956 B2* | 3/2015 | Yoshioka | F01N 13/008 | |
| | | | 73/23.33 | |
| 9,175,586 B2* | 11/2015 | Hashida | F02D 41/1466 | |
| 9,617,899 B2* | 4/2017 | Goodwin | F01N 11/00 | |
| 9,759,675 B2* | 9/2017 | Lee | G01N 15/0656 | |
| 9,803,524 B2* | 10/2017 | Kubinski | F01N 3/027 | |
| 10,018,098 B2* | 7/2018 | Zhang | F01N 3/033 | |
| 2004/0244472 A1* | 12/2004 | Nakamura | G01N 27/4077 | |
| | | | 73/114.75 | |
| 2009/0309571 A1* | 12/2009 | Katsuyama | G01N 15/0656 | |
| | | | 324/71.1 | |
| 2010/0147052 A1* | 6/2010 | Nelson | G01N 15/0656 | |
| | | | 73/28.01 | |
| 2011/0197571 A1* | 8/2011 | Visser | G01N 27/4077 | |
| | | | 60/311 | |
| 2011/0252865 A1* | 10/2011 | Tokuda | G01N 15/0656 | |
| | | | 73/23.31 | |
| 2012/0085146 A1* | 4/2012 | Maeda | G01N 27/043 | |
| | | | 73/23.31 | |
| 2014/0238108 A1* | 8/2014 | Di Miro | G01N 27/04 | |
| | | | 73/28.01 | |
| 2014/0345362 A1* | 11/2014 | Lee | G01N 15/0656 | |
| | | | 73/23.31 | |
| 2015/0168285 A1* | 6/2015 | Hedayat | G01M 15/102 | |
| | | | 73/23.33 | |
| 2015/0177204 A1* | 6/2015 | Bessen | G01N 15/0656 | |
| | | | 73/1.06 | |
| 2016/0017830 A1* | 1/2016 | Wienand | G01N 15/0656 | |
| | | | 73/23.31 | |
| 2016/0103055 A1* | 4/2016 | Gaertner | F01N 11/00 | |
| | | | 73/23.31 | |
| 2016/0223432 A1* | 8/2016 | Kubinski | F01N 3/027 | |
| 2016/0320285 A1* | 11/2016 | Weber | G01N 15/0656 | |
| 2017/0023461 A1* | 1/2017 | Hedayat | G01N 15/0656 | |
| 2017/0045435 A1* | 2/2017 | Sugiyama | G01N 15/0656 | |
| 2017/0058735 A1* | 3/2017 | Zhang | F01N 11/00 | |
| 2017/0131185 A1* | 5/2017 | Koike | G01N 27/04 | |
| 2017/0226972 A1* | 8/2017 | Tsuzuki | G01N 27/4067 | |
| 2017/0298801 A1* | 10/2017 | Zhang | F01N 3/033 | |
| 2017/0307498 A1* | 10/2017 | Sugiyama | G01N 27/60 | |
| 2018/0023431 A1* | 1/2018 | Kubinski | F01N 3/027 | |
| | | | 60/274 | |
| 2018/0238821 A1* | 8/2018 | Otomaru | G01N 27/04 | |

* cited by examiner

CHIP-TYPE PARTICULATE MATTER SENSOR

CROSS-REFERENCE TO RELATED APPLICATIONS

This application claims priority to Korean Patent Application No. 10-2016-0165960, filed on Dec. 7, 2016, which is incorporated herein by reference in its entirety.

BACKGROUND

Field

The present disclosure relates to a PM (Particulate Matter) sensor device for measuring particulate matters contained in exhaust of a vehicle.

Description of Related Art

A vehicle discharges exhaust gas containing a variety of harmful substances, and emissions of the harmful substances are limited through various regulations.

For the limitation, the vehicle includes various sensors for monitoring harmful substances discharged therefrom.

Examples of the various sensors may include a PM (Particulate Matter) sensor for measuring particulate matters contained in exhaust gas. The PM sensor is mounted in an exhaust pipe at the rear of a DPF (Diesel Particulate Filter), and measures the concentration of particulate matters contained in exhaust gas, in order to determine whether the DPF has a trouble.

The disclosure of this section is to provide background of the invention. Applicant notes that this section may contain information available before this application. However, by providing this section, Applicant does not admit that any information contained in this section constitutes prior art.

SUMMARY

An embodiment of the present invention is directed to a chip-type PM sensor of which the sensitivity is not changed, regardless of the mounting direction of a sensing unit.

Another embodiment of the present invention is directed to a chip-type PM sensor capable of reducing a manufacturing cost by reducing the size of a sensing unit.

Other advantages of the present invention can be understood by the following description, and become apparent with reference to the embodiments of the present invention. Also, it is obvious to those skilled in the art to which the present invention pertains that the advantages of the present invention can be realized by the means as claimed and combinations thereof.

In accordance with an embodiment of the present invention, there is provided a chip-type PM sensor including a sensing unit installed in a cylindrical housing mounted on an exhaust pipe, the sensing unit having a sensing pattern for sensing particulate matters contained in exhaust gas. The sensing unit may include: a substrate formed in a direction perpendicular to the longitudinal direction of the housing; and the sensing pattern formed on a surface of the substrate, facing the exhaust pipe, and configured to sense the particulate matters.

The sensing pattern may include a plurality of electrodes patterned in a line shape on the substrate.

The plurality of electrodes forming the sensing pattern may be divided into two or more groups which are not electrically connected to each other, and electrodes of different groups may be alternately arranged.

The plurality of electrodes forming the sensing pattern may be divided into measuring electrodes and ground electrodes, and the measuring electrodes and the ground electrodes may be alternately arranged.

The substrate may have a pad electrode formed on the opposite surface of the surface on which the sensing pattern is formed, the pad electrode being electrically connected to the sensing pattern.

The sensing unit may be patterned in a virtual circle formed in the substrate.

The sensing unit may be fixed in a state where the sensing pattern is exposed to the bottom of an insulator formed in the housing.

The housing may have introduction holes formed at predetermined intervals along the lower circumference thereof, the introduction holes introducing exhaust gas from outside into the housing through a side surface of the housing.

The housing may have partitions formed therein, the partitions guiding the exhaust gas introduced into the housing to the sensing unit.

The partitions may be formed in a plate shape, and arranged in the circumferential direction of the housing.

The introduction hole may be formed between the adjacent partitions.

The housing may have a drain hole formed at the bottom thereof, the drain hole discharging condensate water of the housing.

DESCRIPTION OF EMBODIMENTS

Hereafter, a chip-type PM (Particulate Matter) sensor in accordance with an embodiment of the present invention will be described in detail with reference to the accompanying drawings.

Figure 1:
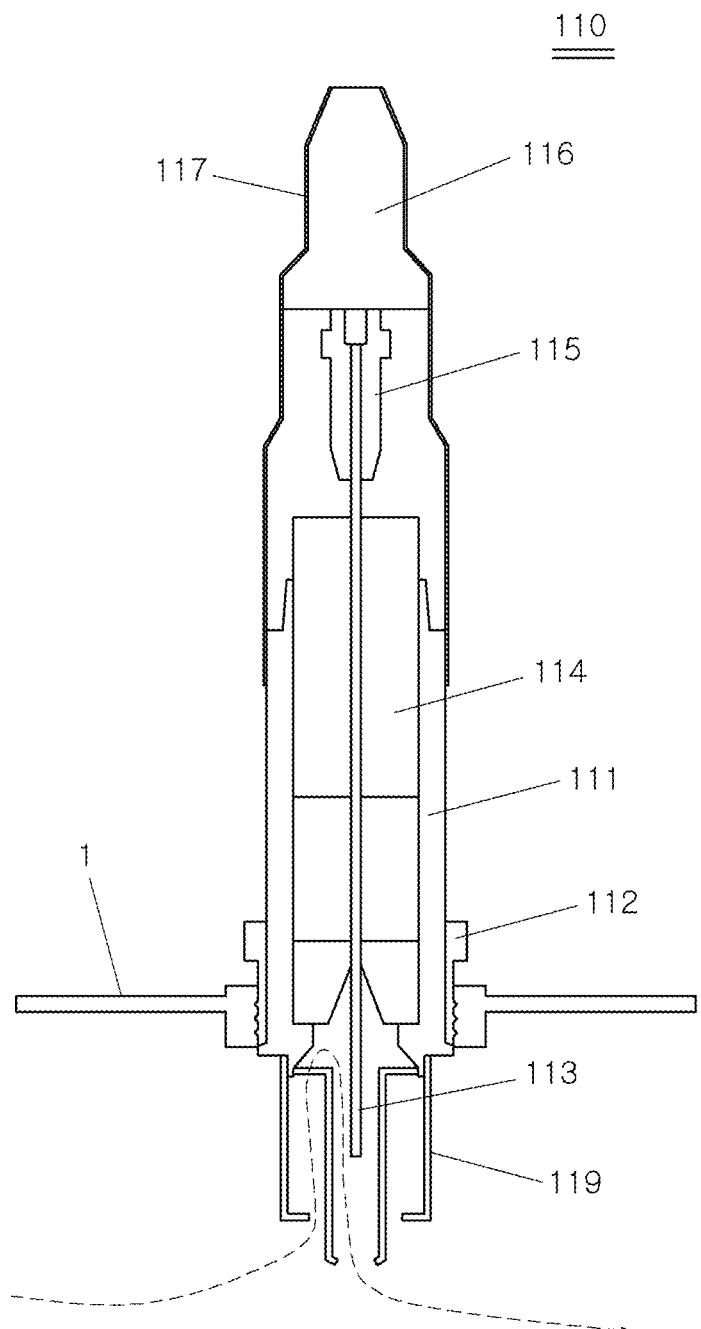
FIG. 1 is a cross-sectional view illustrating a typical PM (Particulate Matter) sensor.

Referring to FIG. 1 illustrating the structure of a typical PM sensor 110, a sensing unit 113 is mounted in a housing 111. The housing 111 is fixed to an exhaust pipe 1 by a fixing nut 112, and includes an insulator 114 installed therein so as to insulate the sensing unit 113. The upper end of the sensing unit 113 is fixed by a clam shell 115. The PM sensor 110 has Teflon (PTFE) 116 formed at the upper end thereof, and the upper end of the PM sensor 110 is covered by a cap 117. The lower end of the sensing unit 113 is exposed to flowing exhaust gas, and a protective tube 119 is coupled to the lower end of the housing 111 such that the exhaust gas flowing through the exhaust pipe 1 is introduced into the sensing unit 113.

The exhaust gas flowing through the exhaust pipe 1 is introduced into one side of the protective tube 119, and then reaches the sensing unit 113. Since the sensing unit 113 is formed in a bar shape, different values may be measured depending on the mounting direction of the sensing unit 113. The sensing unit 113 has a sensing pattern 113b formed at an end of a substrate 113a so as to sense the particulate materials. The substrate 113a is installed in a direction perpendicular to the exhaust gas flow.

Figure 2:
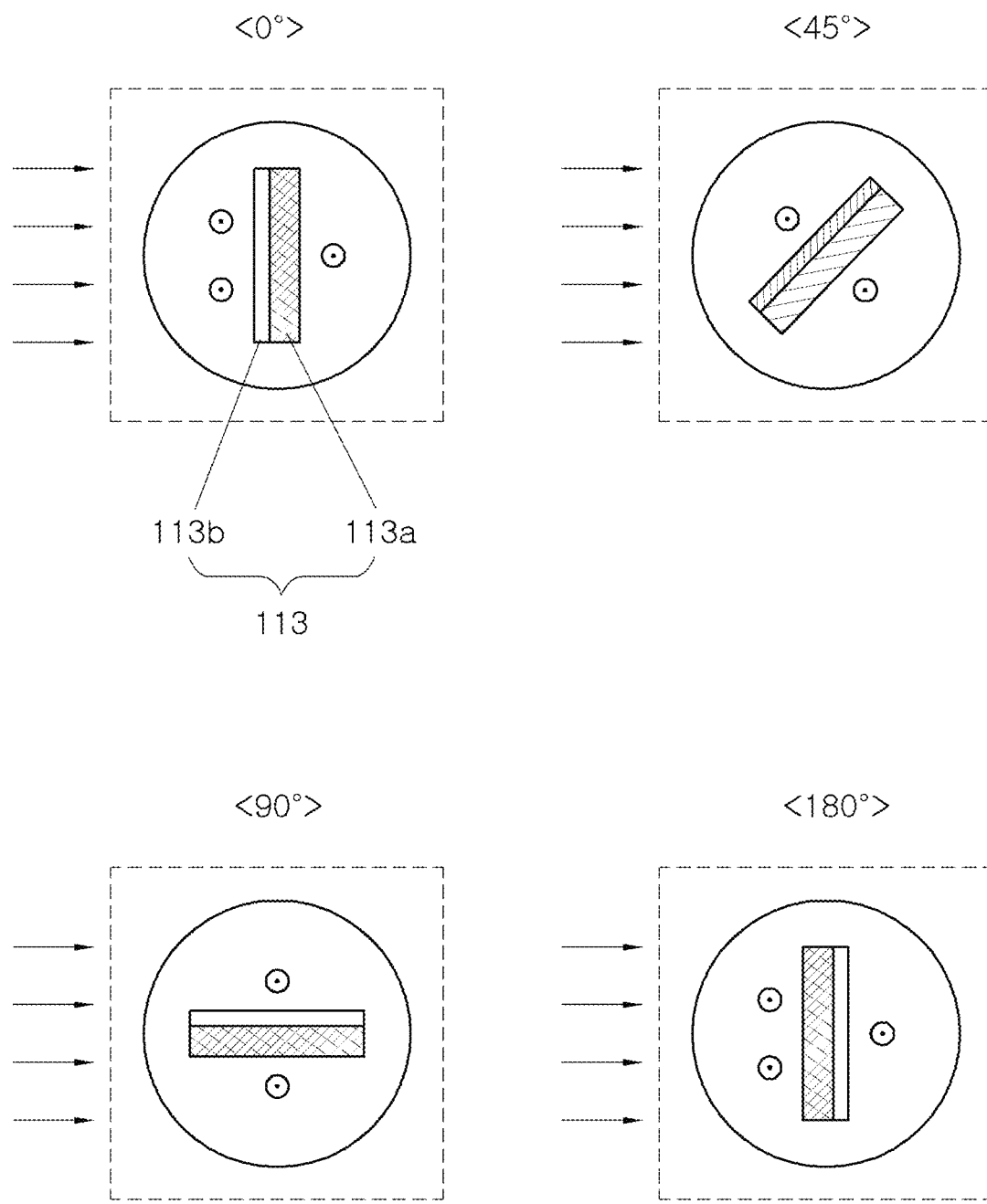
FIG. 2 is a diagram for describing changes in sensitivity of the PM sensor shown in FIG. 1, depending on an installation direction of a sensing unit.

As illustrated in FIG. 2, the sensing unit 113 may be disposed at various angles which are not perpendicular to the exhaust gas, compared to when the sensing unit 113 is disposed at a regular position (0°). Then, the sensitivity of the sensing unit 113 may be degraded depending on the angles. FIG. 2 illustrates exhaust gas flows when the sensing unit 113 is disposed at the regular position (0°), 45°, 90° and 180°. When the sensing unit 113 is mounted at a predetermined angle in comparison to when the sensing unit 113 is disposed at the regular position, the flow rate of exhaust gas flowing along the surface of the sensing pattern 113b decreases to reduce the sensitivity. As the mounting angle is increased more than at the regular position, the flow rate of exhaust gas flowing along the surface of the sensing pattern 113b decreases. As such, since the PM sensor 110 has different sensitivities depending on the mounting position of the sensing unit 113, the reliability of the PM sensor 110 is lowered.

Figure 3:
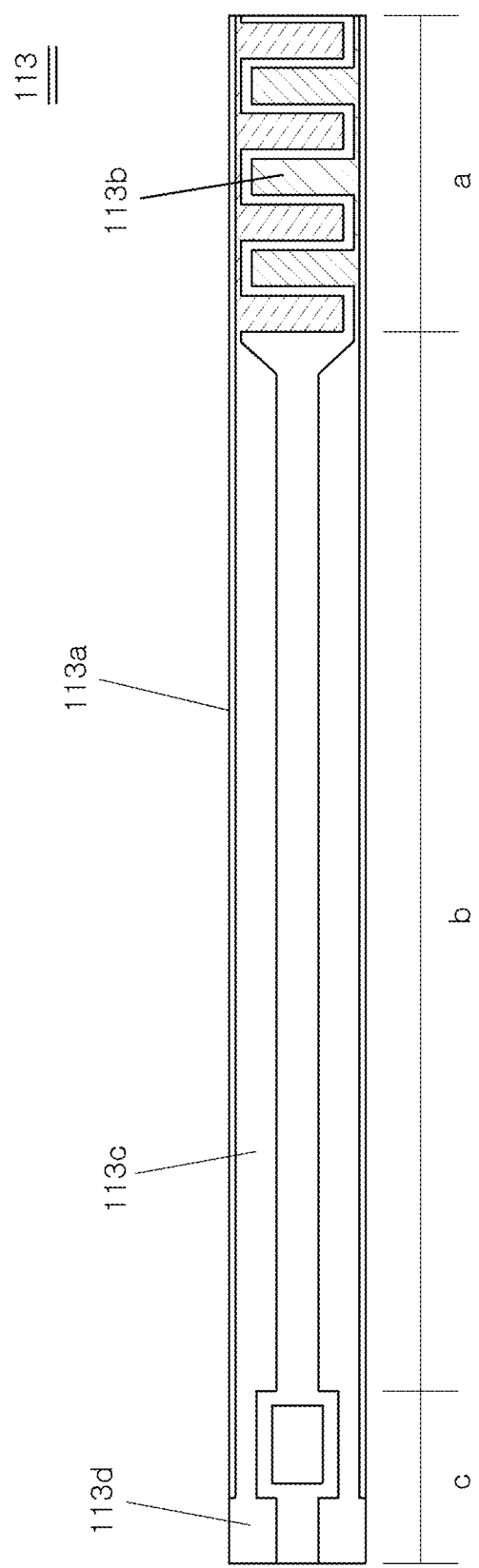
FIG. 3 is a plan view illustrating the sensing unit in the PM sensor shown in FIG. 1.

Furthermore, as illustrated in FIG. 3, the sensing unit 113 has a structure in which the sensing pattern 113b and a pad electrode 113d are separated far away from each other. Thus, the sensing pattern 113b and the pad electrode 113d are connected through a signal line 113c. At this time, since the signal line 113c requires quite a long length, a large amount of expensive platinum (Pt) is used. The signal line 113c needs to be formed across a section B between a section A in which the sensing pattern 113b is formed and a section C in which the pad electrode 113d is formed. Thus, in order to form the signal line 113c, a large amount of Pt is used.

Furthermore, since the sensing pattern 113b and the pad electrode 113d are separated far away from each other, the number of sensing units 113 manufactured from the same area of sheet may decrease.

Referring to FIGS. 5-13, in embodiments, the chip-type PM sensor in accordance with the embodiment of the present invention includes a sensing unit 13 installed in a housing 11, the sensing unit 13 being disposed in a direction perpendicular to the longitudinal direction of the housing 11.

Figure 5:
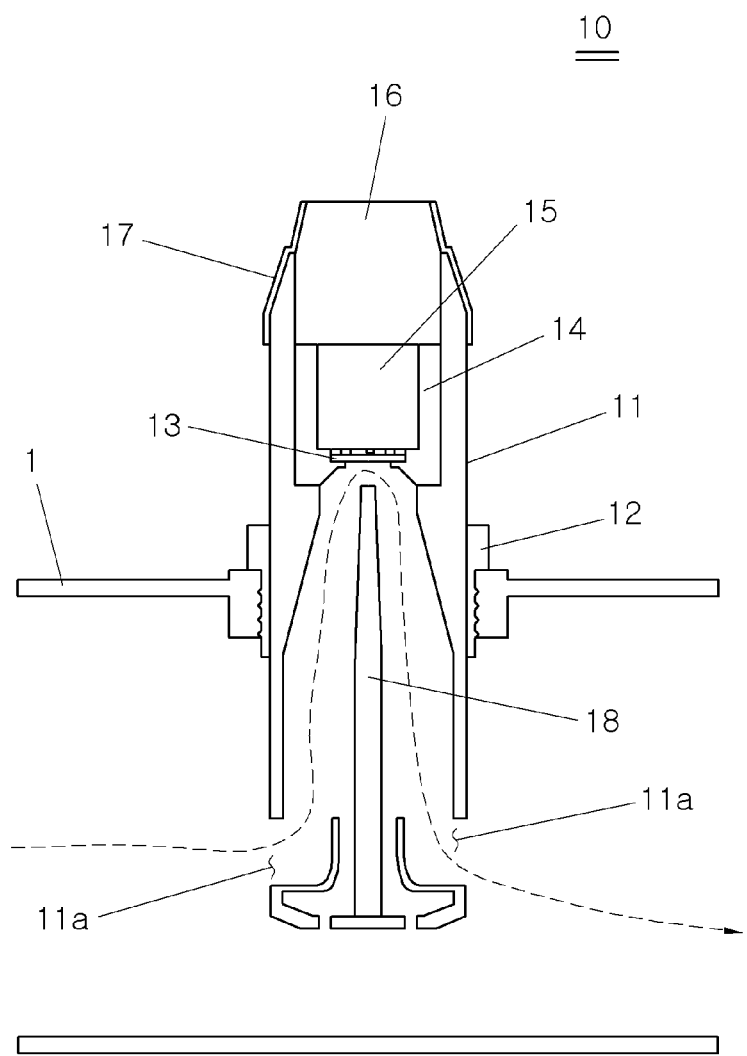
FIG. 5 is a cross-sectional view of a chip-type PM sensor in accordance with an embodiment of the present invention.
Figure 6:
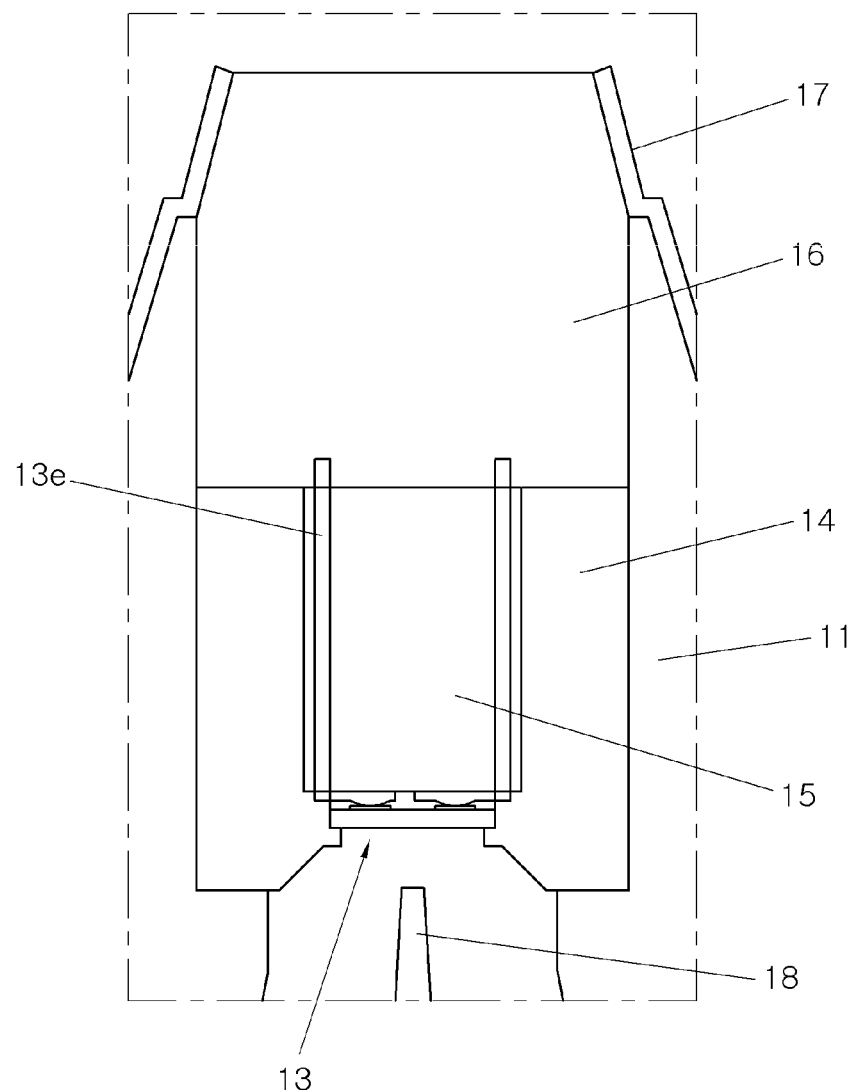
FIG. 6 is a cross-sectional view illustrating a portion where a sensing unit is installed in the chip-type PM sensor in accordance with the embodiment of the present invention.
Figure 7:
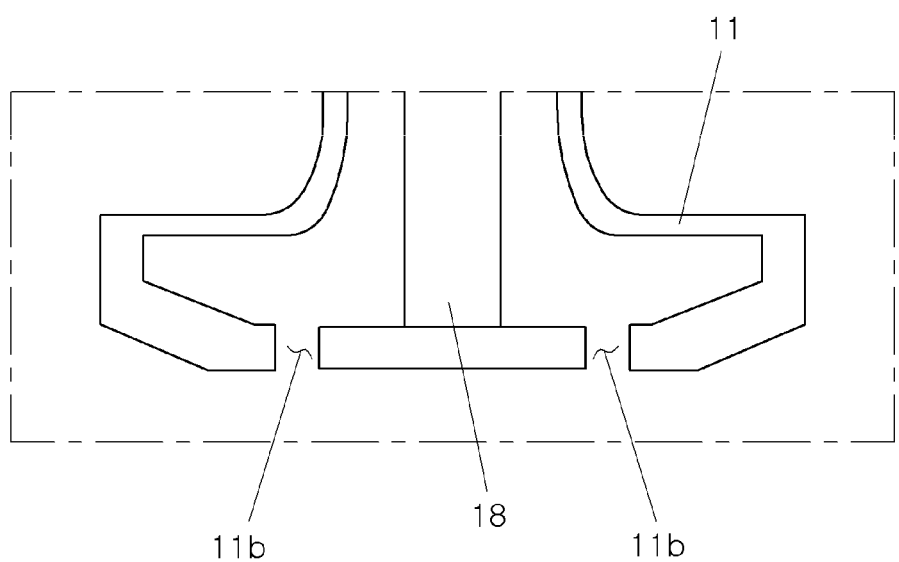
FIG. 7 is a cross-sectional view illustrating a lower portion of the chip-type PM sensor in accordance with an embodiment of the present invention.
Figure 8:
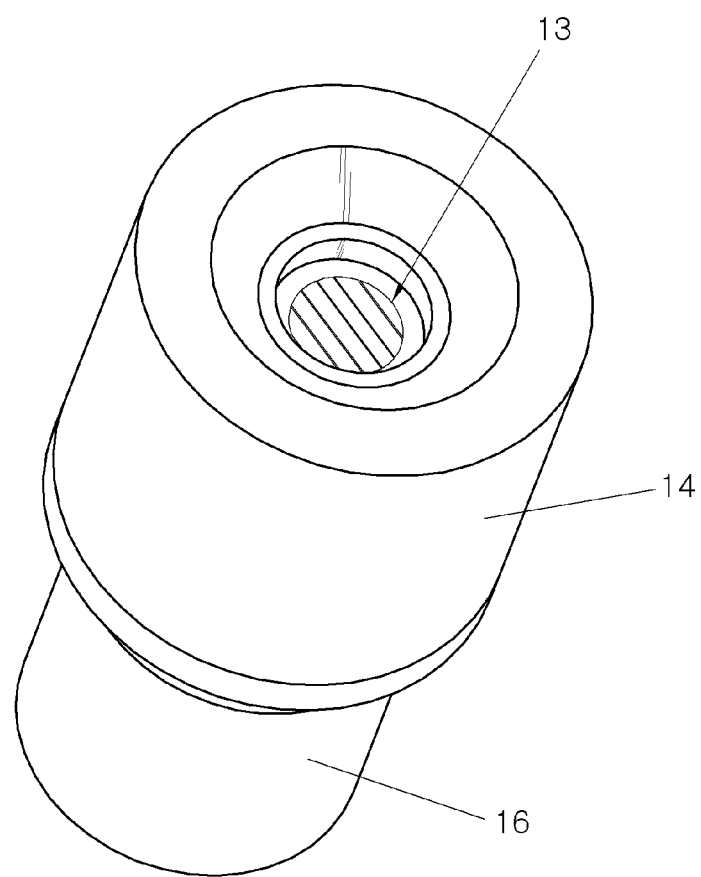
FIG. 8 is a bottom perspective view illustrating a state in which the sensing unit is installed in an insulator in the chip-type PM sensor in accordance with the embodiment of the present invention.
Figure 9:
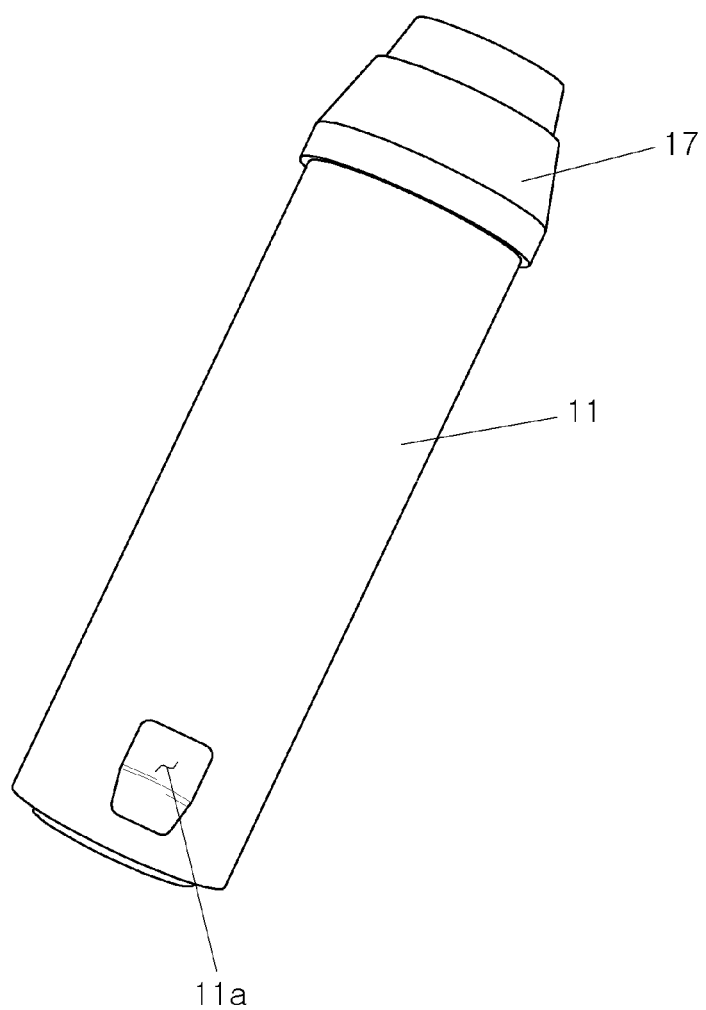
FIG. 9 is an external perspective view of the chip-type PM sensor in accordance with the embodiment of the present invention.
Figure 10:
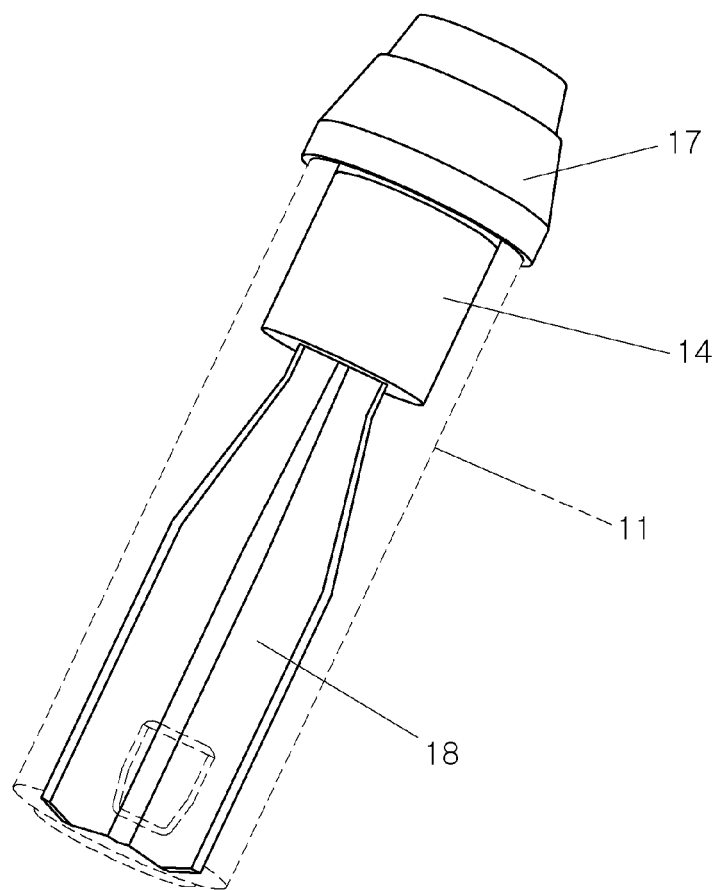
FIG. 10 is a projected perspective view of the chip-type PM sensor in accordance with the embodiment of the present invention.

FIG. 5 illustrates the chip-type PM sensor 10 in accordance with the embodiment of the present invention.

The housing 11 is vertically fixed to an exhaust pipe 1 through which exhaust gas flows. The housing 11 is formed in a hollow cylindrical shape. The housing 11 is fixed to the exhaust pipe 1 through a fixing nut 12 fixed to the outside of the housing 11.

The housing 11 has a plurality of exhaust intake/discharge holes 11a formed along the circumference thereof. Some of the hole 11a serve to introduce or intake the exhaust gas into the housing 11 or the other holes 11a serve to discharge the exhaust out of the housing 11.

The housing 11 may have a drain hole 11b formed at the bottom thereof, such that water condensed in the housing 11 can be discharged to the outside through the drain hole 11b.

The sensing unit 13 is installed in the housing 11 along a direction perpendicular to the longitudinal direction of the housing 11, in embodiments, a direction parallel to the exhaust pipe 1. The exhaust gas introduced through the hole 11a flows toward the sensing unit 13, and the sensing unit 13 measures particulate matters contained in the exhaust gas.

The insulator 14 is formed in the housing 11 so as to install the sensing unit 13. The sensing unit 13 is fixed and installed at the bottom of the insulator 14. Specifically, the sensing unit 13 is installed at the insulator 14 such that a portion of the sensing unit 13, where a sensing pattern 13b is formed, is exposed to the bottom of the insulator 14. The insulator 14 serves to insulate the sensing unit 13 from the housing 11.

A clam shell 15 is positioned in the insulator 14, and a terminal 13e is installed through the clam shell 15 and connected to the sensing unit 13.

The clam shell 15 has Teflon 16 formed at the top thereof, and a cap 17 is formed outside the uppermost end of the PM sensor 10.

A plurality of partitions 18 are formed in the housing 11. The partitions 18 are formed from the middle portion toward the bottom of the housing 11. The partitions 18 are formed in a plate shape and arranged along the circumferential direction of the housing 11. The partitions 18 may be arranged at even intervals. Between the adjacent partitions 18, the hole 11a may be disposed. The lower ends of the partitions 18 are fixed to the bottom of the housing 11. The exhaust gas introduced into the housing 11 through the hole 11a does not flow along the circumferential direction of the housing 11 due to the partition 18, but flows toward the top of the housing 11 and then flows in the direction parallel to the exhaust pipe 1 while flowing over the upper end of the partition 18. At this time, the exhaust gas passes through the sensing unit 13.

The sensing unit 13 will be described in detail as follows.

The sensing unit 13 has the sensing pattern 13b formed on one surface of a substrate 13a and a pad electrode 13d formed on the other surface of the substrate 13a. The sensing pattern 13b comes in contact with the exhaust gas, and the pad electrode 13d is electrically connected to the terminal 13e while being electrically connected to the sensing pattern 13b.

The sensing pattern 13b is formed on the surface of the substrate 13a, facing the exhaust pipe 1, through patterning. The sensing pattern 13b includes a plurality of electrodes formed in a line shape. The electrodes of the sensing pattern 13b are divided into two or more groups which are not electrically connected to each other, and electrodes of different groups are alternately arranged. Furthermore, electrodes of the same group are electrically connected to each other.

For example, when the electrodes are divided into measuring electrodes and ground electrodes, the measuring electrodes and the ground electrodes are alternately arranged, and the measuring electrodes are not electrically connected to the ground electrodes. Furthermore, the measuring electrodes are electrically connected to each other, and the ground electrodes are electrically connected to each other.

Figure 11:
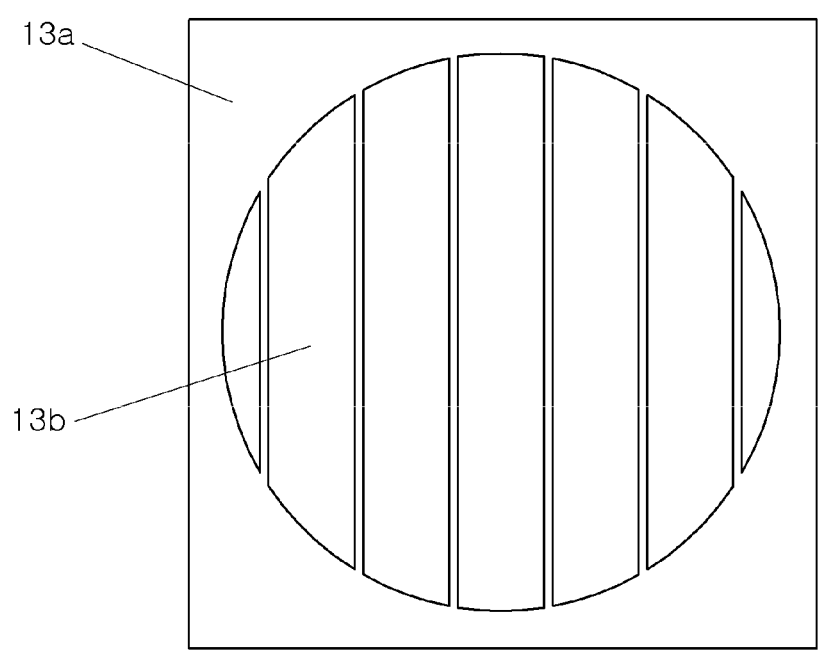
FIG. 11 is a plan view illustrating a sensing pattern of the chip-type PM sensor in accordance with an embodiment of the present invention.
Figure 12:
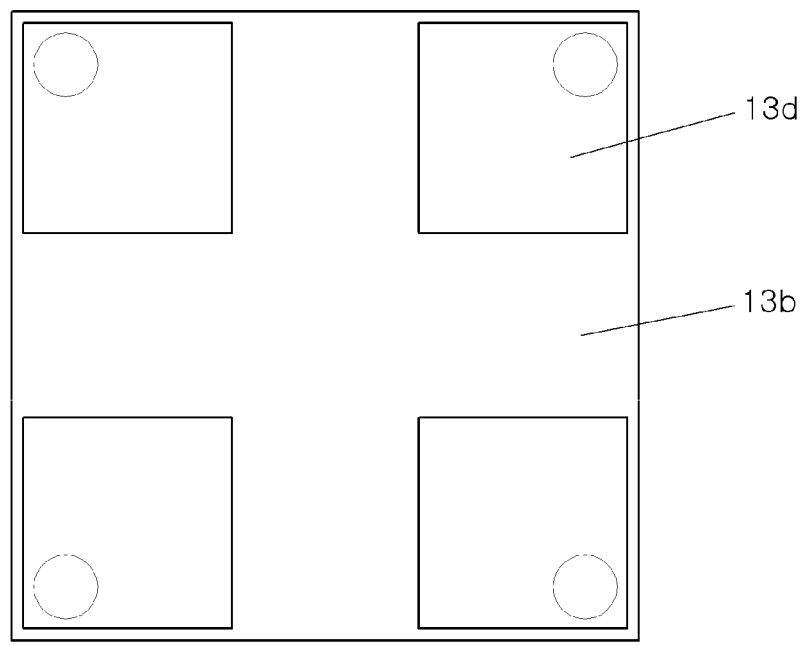
FIG. 12 is a plan view illustrating a pad electrode of the chip-type PM sensor in accordance with the embodiment of the present invention.

The sensing pattern 13b of the sensing unit 13 is formed in a virtual circle formed in the substrate 13a (refer to FIG. 11).

The sensing unit 13 may be manufactured by patterning the sensing unit 13 in a preset size of ceramic sheet 20 along rows and columns. In embodiments, after the sensing units 13 are repetitively patterned in the ceramic sheet 20 along rows and columns as illustrated in FIG. 13, the sensing units 13 may be cut into individual sensing units 13.

In the present embodiment, the circular sensing pattern 13b is formed in the sensing unit 13, and the sensing pattern 13b and the pad electrode 13d are formed on the front and rear surfaces of the substrate 13a. Thus, since the signal line for connecting the sensing pattern and the pad electrode is not needed, the amount of expensive platinum (Pt) can be reduced. Although the area of the sensing pattern 13b is increased more than in the typical sensor device discussed above, the amount of Pt used in the signal line can be significantly reduced. Thus, the entire amount of Pt can be reduced.

Furthermore, the number of sensing units 13 formed in the ceramic sheet 20 having the same area may be increased more than in the typical sensor device discussed above.

Figure 4:
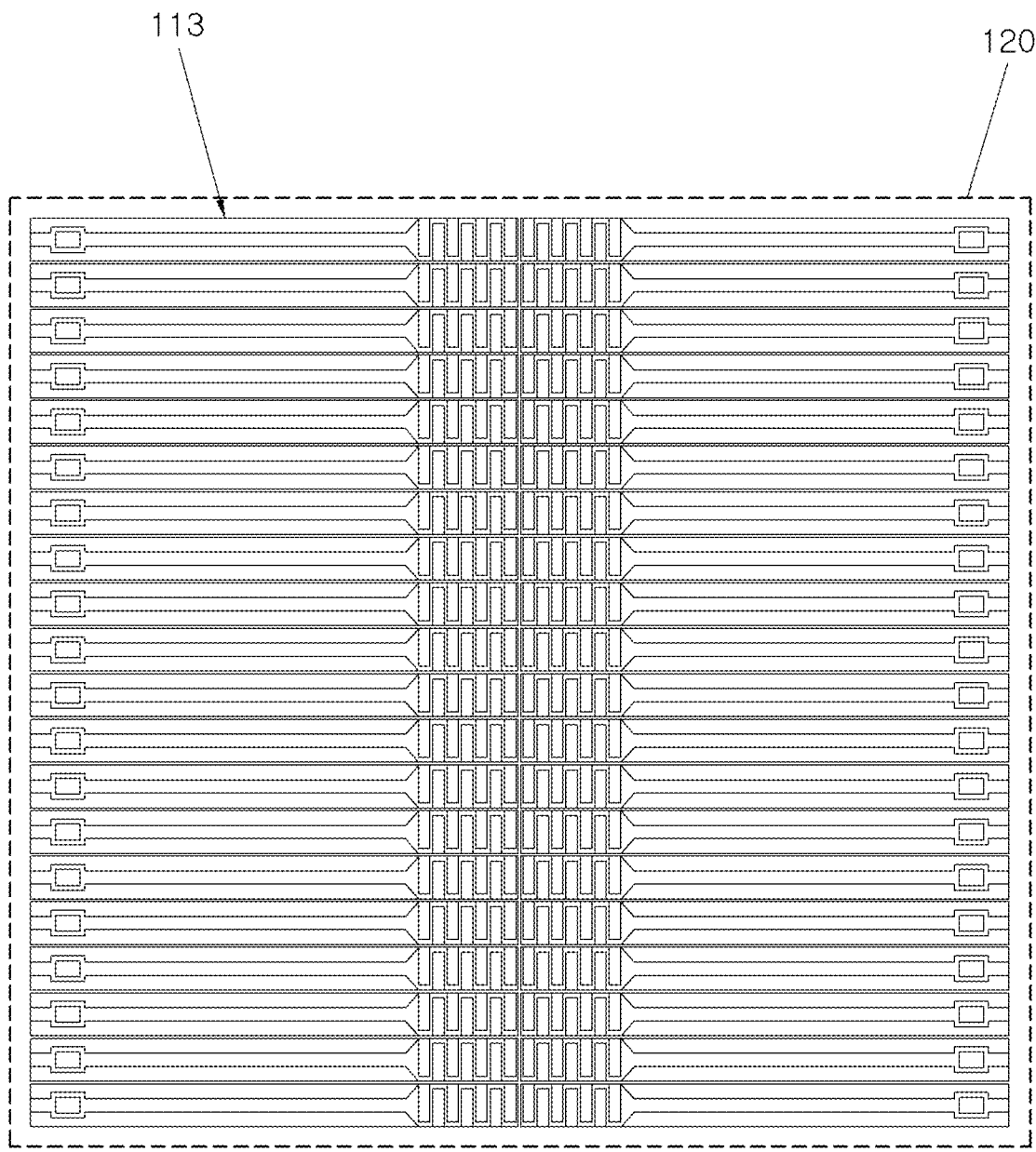
FIG. 4 is a plan view illustrating a state in which sensing units of the PM sensor shown in FIG. 1 are patterned in a ceramic sheet.
Figure 13:
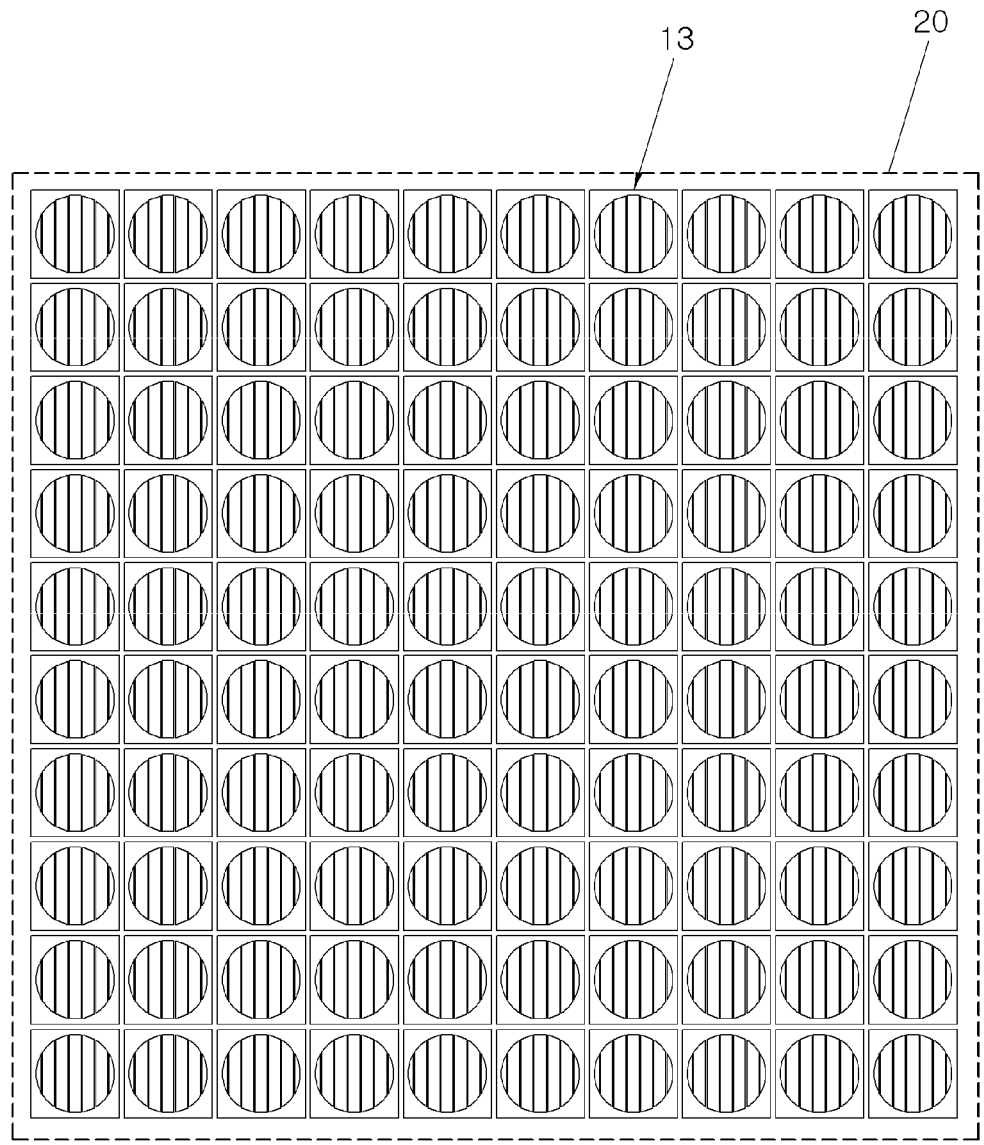
FIG. 13 is a plan view illustrating a state in which the sensing units of the chip-type PM sensor in accordance with the embodiment of the present invention are patterned in a ceramic sheet.

For example, suppose that the ceramic sheets 20 and 120 illustrated in FIGS. 4 and 13, respectively, have the same size of 100 mm×100 mm. In this case, while 40 sensing units are formed in the typical sensor device discussed above (refer to FIG. 4), 100 sensing units 13 can be formed in the present embodiment. In FIG. 4, when the sensing pattern has a size of 4 mm×10 mm, two sensing units are formed in the horizontal direction, and 20 sensing units are formed in the vertical direction, while forming a distance from adjacent sensing patterns. Thus, a total of 40 sensing units are formed, and the area of each sensing unit becomes 40 mm². On the other hand, in the present embodiment, 10 sensing patterns having a diameter of 4 mm can be formed in the horizontal and vertical directions, and the area of each sensing pattern 13b becomes approximately 50.24 mm²($\pi$×4 mm²).

Thus, since no signal lines are required, the area of the sensing pattern 13b in the sensing unit 13 is increased, the amount of Pt used to form the pattern in each of the sensing units 13 is reduced, and the size of the sensing unit 13 is also reduced.

In accordance with the embodiments of the present invention, since the chip-type PM sensor includes the chip-type sensing unit, the sensitivity can be constantly maintained regardless of the mounting direction.

Furthermore, although the area of the sensing unit is slightly increased, no signal line is required. Thus, the amount of Pt used in the sensing unit is reduced.

Furthermore, a larger number of sensing units can be manufactured from a ceramic sheet having the same area.

In embodiments, referring to FIGS. 5-10, a PM (Particulate Matter) sensor device 10 is installed on the exhaust pipe 1 through which exhaust containing gas and particulate matters flows along a flow direction. The pipe 1 includes an engaging hole for receiving the sensor device 10 and the engaging hole has a threaded inner wall, while the device 10 has a threaded wall. Thus, when installing the device 10 on the pipe 1 by inserting the device 10 in a direction perpendicular to the flow direction and rotating the device 10 with respect to the pipe 1, the threaded outer wall of the device 10 and the threaded inner wall of the hole are engaged with each other.

The PM device 10 includes a housing 11 having a cylindrical wall extending into the pipe generally in a direction perpendicular to the flow direction. The PM device 10 further includes a sensing unit 13 installed in the housing for sensing particular matters contained in exhaust. The sensing unit 10 includes a sensing surface with a sensing pattern 13b. The sensing unit 13 is arranged and mounted in the housing 11 such that the sensing surface of the sensor unit 13 generally parallel to the flow direction. Thus, the sensing surface maintains the same orientation relative to the flowing direction regardless how much the device 10 is rotated with respect to the pipe 1 for engaging the threaded walls.

In embodiments, the housing 11 has a plurality of holes 11a formed on the wall for receiving/discharging the exhaust. The device 10 includes a plurality of partition walls 18 formed in the housing 11. In one embodiment, the plurality of partition walls 18 include three or more walls extending radially and arranged angularly for providing a plurality of channels in the housing. In embodiments, each channel is formed by two immediately neighboring partition walls 18 and the housing wall. In one embodiment, each channel has a portion extending generally perpendicular to the flow direction. The sensing surface is spaced from the partition walls such that the exhaust can flow between the sensing surface and the partition walls 18. In embodiments, while a portion of the exhaust received through a hole 11a into the housing flows through one of the channels toward the sensing surface, a space between the sensing surface and the partition walls and another channel, the sensor 13 detects the particular matters contained in the exhaust flowing inside the housing. The exhaust is discharged through another hole 11a. For each channel, a single hole 11a or two or more holes 11a are formed.

While embodiments of the present invention have been described, it will be apparent to those skilled in the art that various changes and modifications may be made without departing from the spirit and scope of the invention as defined in the following claims.

What is claimed is:

1. A PM (Particulate Matter) sensor apparatus comprising:
a housing to be coupled to an exhaust pipe; and
a sensor installed in the housing, the sensor having a sensing pattern for sensing particulate matters contained in exhaust gas,
wherein the housing further comprises a cylindrical wall and a plurality of radial partition walls located inside the cylindrical wall,
wherein the cylindrical wall comprises a plurality of holes arranged in a predetermined interval along a circumference of the cylindrical wall such that, through the plurality of holes, exhaust gas is introduced into and discharged from the housing,
wherein the plurality of radial partition walls are arranged in a predetermined angular interval along the circumference of the cylindrical wall and meet at the center of the housing to form a plurality of channels extending along a longitudinal direction of the housing such that the exhaust gas flows in the longitudinal direction through the plurality of channels, wherein the sensing pattern is formed on a sensing surface of the sensor that is arranged to face in the longitudinal direction toward the plurality of channels such that the exhaust gas flowing through the plurality of channels reaches the sensing pattern, wherein the sensing pattern comprises a plurality of electrodes patterned in a line shape on a substrate of the sensor, wherein the plurality of electrodes forming the sensing pattern are divided into two or more groups which are not electrically connected to each other, and electrodes of different groups are alternately arranged, wherein the plurality of electrodes forming the sensing pattern is patterned in a same substrate of the sensor, wherein the sensor is fixed in a state where the sensing pattern is exposed to the bottom of an insulator formed in the housing, and wherein the sensing pattern is exposed toward lower end of the housing.

2. The PM sensor apparatus of claim 1, wherein the plurality of electrodes forming the sensing pattern are divided into measuring electrodes and ground electrodes, and the measuring electrodes and the ground electrodes are alternately arranged.

3. The PM sensor apparatus of claim 1, wherein the substrate has a pad electrode formed on the opposite surface of the sensing surface on which the sensing pattern is formed, the pad electrode being electrically connected to the sensing pattern.

4. The PM sensor apparatus of claim 1, wherein the sensor is patterned in a virtual circle formed in the substrate.

5. The PM sensor apparatus of claim 1, wherein each of the plurality holes is formed between immediately neighboring two of the plurality of partition walls.

6. The PM sensor apparatus of claim 1, wherein the housing has a drain hole formed at the bottom thereof such that condensate water of the housing is discharged through the drain hole.

* * * * *